United States Patent [19]

Petersen et al.

[11] Patent Number: 4,559,342

[45] Date of Patent: Dec. 17, 1985

[54] QUINOLONE ACIDS AND ANTIBACTERIAL AGENTS CONTAINING THESE COMPOUNDS

[75] Inventors: Uwe Petersen, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 576,596

[22] Filed: Feb. 3, 1984

[30] Foreign Application Priority Data

Feb. 25, 1983 [DE] Fed. Rep. of Germany ....... 3306772

[51] Int. Cl.[4] .................. A61K 31/495; C07D 401/04
[52] U.S. Cl. ..................................... 514/254; 544/358; 544/363; 546/156
[58] Field of Search ....................... 544/363; 424/251; 514/254

[56] References Cited

U.S. PATENT DOCUMENTS

| | | | |
|---|---|---|---|
| 3,149,104 | 9/1964 | Lesher et al. | 544/363 |
| 3,590,036 | 6/1971 | Lesher et al. | 544/363 |
| 4,017,622 | 4/1977 | Minami et al. | 544/363 |

FOREIGN PATENT DOCUMENTS

| | | | |
|---|---|---|---|
| 3306771 | 8/1984 | Fed. Rep. of Germany | 544/363 |
| 3306772 | 8/1984 | Fed. Rep. of Germany | 544/363 |

*Primary Examiner*—Glennon H. Hollrah
*Assistant Examiner*—James H. Turnipseed
*Attorney, Agent, or Firm*—Sprung, Horn, Kramer & Woods

[57] ABSTRACT

The invention relates to quinolone carboxylic acids of the formula (I) as defined herein, pharmaceutical compositions containing said quinolone carboxylic acids and the use of said compounds and compositions for treatment of bacterial infection. Also included in the invention are process for the manufacture of the active quinolone carboxylic acids.

15 Claims, No Drawings

QUINOLONE ACIDS AND ANTIBACTERIAL AGENTS CONTAINING THESE COMPOUNDS

The present invention relates to quinolonecarboxylic acids, processes for their preparation and antibacterial agents containing these compounds.

It has been found that the new quinolonecarboxylic acids of the formula (I)

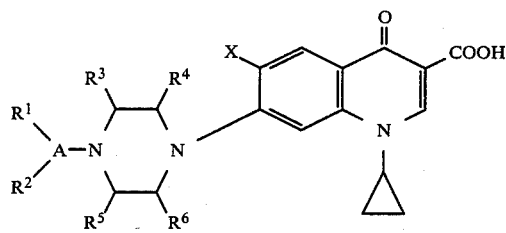

in which

A represents straight-chain or branched alkylene with 1 to 6 carbon atoms or a radical >C=CH—, $R^1$ represents alkoxycarbonyl with 1 to 6 carbon atoms in the alkyl part, benzyloxycarbonyl, carboxyl, optionally substituted carbamoyl, cyano, dialkoxyphosphonyl or alkylsulphonyl with 1 to 4 carbon atoms in the alkyl part and $R^2$ represents hydrogen, alkoxycarbonyl with 1 to 6 carbon atoms in the alkyl part, benzyloxycarbonyl, optionally substituted carbamoyl, cyano, chlorine, acetyl, alkyl with 1 to 3 carbon atoms or phenyl, or $R^1$ and $R^2$, together with the carbon atom which joins them form a 2-oxo-tetrahydrofuryl ring, and $R^3$, $R^4$, $R^5$ and $R^6$ are identical or different and represent hydrogen, methyl, ethyl or n- or i-propyl and X represents hydrogen, halogen, preferably fluorine or chlorine, or nitro, and pharmaceutically useful acid addition, alkali metal and alkaline earth metal salts and hydrates thereof, have a good antibacterial action both against Gram-positive and against Gram-negative bacteria.

Preferred compounds of the formula (I) are those in which the symbols have the following meanings:

A=straight-chain or branched alkylene with 1 to 5 C atoms or >C=CH—, $R^1$=alkoxycarbonyl with 1 to 5 C atoms in the alkyl part, benzyloxycarbonyl, carboxyl, carbamoyl which is optionally substituted by 1 or 2 methyl or ethyl radicals, cyano, methylsulphonyl or ethylsulphonyl and $R^2$=hydrogen, alkoxycarbonyl with 1 to 5 C atoms in the alkyl part, benzyloxycarbonyl, carbamoyl, cyano, chlorine, acetyl, alkyl with 1 or 2 carbon atoms or phenyl, or $R^1$ and $R^2$, together with the C atom which joins them form a 2-oxo-tetrahydrofuryl ring, $R^3$, $R^4$, $R^5$ and $R^6$=hydrogen, methyl or ethyl and X=hydrogen, fluorine, chlorine or nitro.

Particularly preferred compounds of the formula (I) are those in which the symbols have the following meanings:

A=straight-chain alkylene with 1 to 5 C atoms or >C=CH—, $R^1$=alkoxycarbonyl with 1 to 4 C atoms in the alkyl part, benzyloxycarbonyl, carboxyl, carbamoyl, cyano or methylsulphonyl and $R^2$=hydrogen, alkoxycarbonyl with 1 to 3 C atoms in the alkyl part, cyano, chlorine, acetyl or phenyl, or $R^1$ and $R^2$, together with the C atom which joins them form a 2-oxo-tetrahydro-3-furyl ring, $R^3$=hydrogen, methyl or ethyl, $R^4$=hydrogen, $R^5$=hydrogen or methyl, $R^6$=hydrogen and X=hydrogen, fluorine, chlorine or nitro.

It has furthermore been found that the compounds of the formula (I) according to the invention are obtained by a process in which a compound of the formula (II)

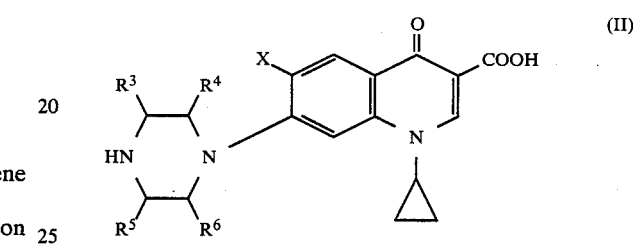

in which X, $R^3$, $R^4$, $R^5$ and $R^6$ have the abovementioned meaning, is reacted with a compound of the formula (III)

in which $R^1$, $R^2$ and A have the abovementioned meaning and

Y represents halogen, preferably chlorine, bromine or iodine, $CH_3O$—$SO_2$—O, $C_2H_5O$—$SO_2$—O, methoxy or ethoxy (method A).

Compounds of the formula (I) according to the invention are also obtained by a process in which compounds of the formula (II)

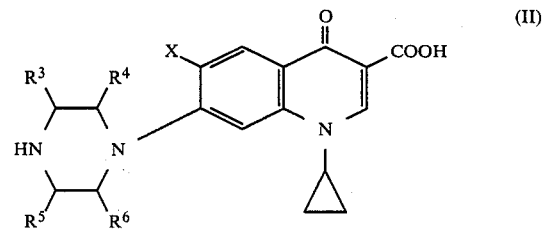

are reacted with compounds of the formula (IV)

in which $R^1$ and $R^2$ have the abovementioned meaning, compounds of the formula (Ia) according to the invention (I; A=>CH—$CH_2$—)

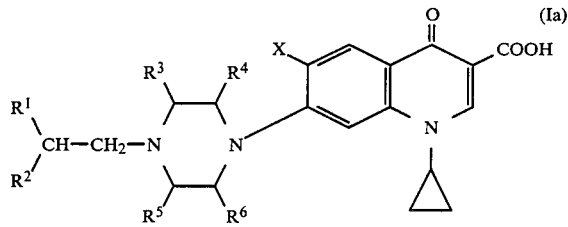

being formed (method B).

Compounds of the formula (I) according to the invention are also obtained by a process in which compounds of the formula (V)

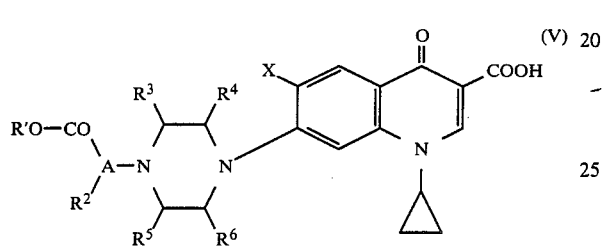

in which $R^2$, $R^3$, $R^4$, $R^5$, $R^6$ and X have the abovementioned meaning and R' represents alkyl with 1 to 6 carbon atoms or benzyl, are reacted under alkaline or acid conditions or, if R'=benzyl, also under hydrogenolytic conditions, compounds of the formula (Ib) according to the invention=(I, $R^1$=COOH)

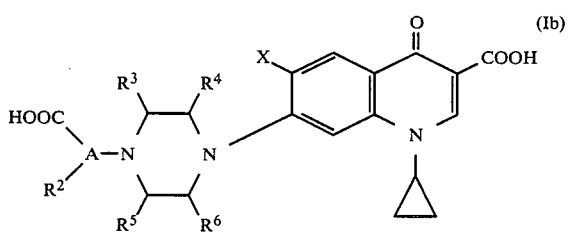

being formed (method C).

Surprisingly, the quinolonecarboxylic acids according to the invention display a considerably more powerful antibacterial action than the known compound 1-ethyl-6-fluoro-1,4-dihydro-4-oxo-7-(1-piperazinyl)-3-quinolinecarboxylic acid (norfloxacin). The substances according to the invention thus represent an enrichment of pharmacy.

If, for example, 1-cyclopropyl-6-fluoro-1,4-dihydro-4-oxo-7-(1-piperazinyl)-3-quinolinecarboxylic acid and ethyl bromoacetate are used as starting compounds in the reaction of (II) with (III) according to method A, the course of the reaction can be represented by the following equation:

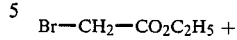

$Br-CH_2-CO_2C_2H_5 +$

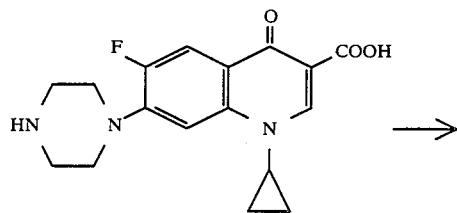

If, for example, 1-cyclopropyl-6-fluoro-1,4-dihydro-4-oxo-7-(1-piperazinyl)-3-quinolinecarboxylic acid and acrylonitrile are used as starting substances in the reaction of (II) with (IV) according to method B, the course of the reaction can be represented by the following equation:

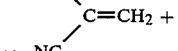

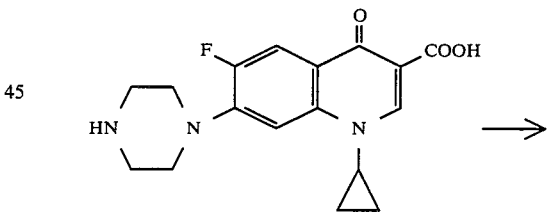

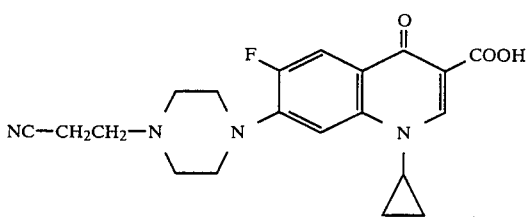

If, for example, 1-cyclopropyl-7-(4-ethoxycarbonylmethyl-1-piperazinyl)-6-fluoro-1,4-dihydro-4-oxo-3-quinolinecarboxylic acid and sulphuric acid are used as starting compounds in the hydrolysis of (V) according to method C, the course of the reaction can be represented by the following equation:

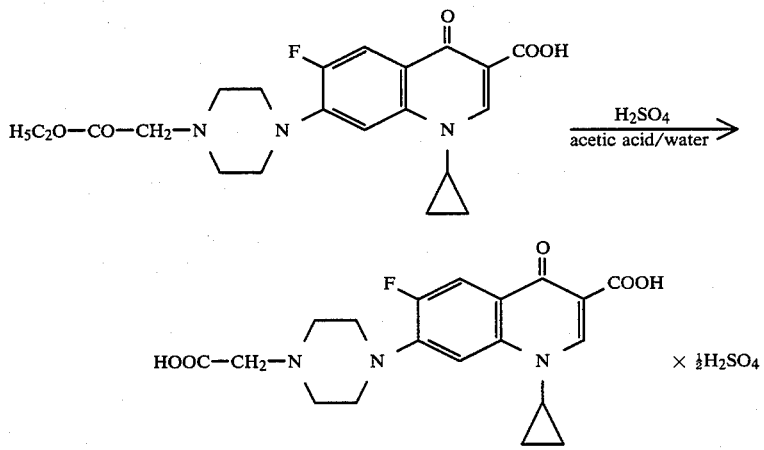

The compounds of the formula (II) used as starting compounds can be prepared by reacting compounds of the formula (VI)

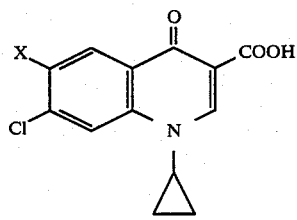

with piperazine or piperazine derivatives of the formula (VII)

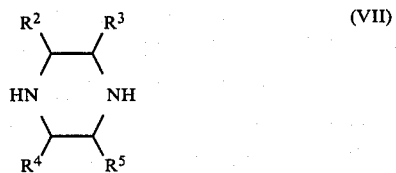

This reaction is carried out in a diluent, such as dimethylsulphoxide, hexamethylphosphoric acid triamide, sulpholane, water, an alcohol or pyridine, at temperatures from 20° to 200° C., preferably at 80° to 180° C. In carrying out the process, 1 to 15 moles of the compound VII, preferably 1 to 6 moles of the compound VII, are employed per mole of carboxylic acid VI. If equivalent amounts of the carboxylic acid VI and the piperazine derivative VII are used, the reaction is carried out in the presence of an acid-binding agent, for example triethylamine, 1,4-diaza-bicyclo[2,2,2]octane or 1,8-diazabicyclo[5,4,0]undec-7-ene.

Examples which may be mentioned of the starting substances of the formula (II) which can be prepared in this manner are: 1-cyclopropyl-6-fluoro-1,4-dihydro-4-oxo-7-(1-piperazinyl)-3-quinolinecarboxylic acid, 1-cyclopropyl-6-fluoro-1,4-dihydro-4-oxo-7-(2,5-dimethyl-1-piperazinyl)-3-quinolinecarboxylic acid, 1-cyclopropyl-6-fluoro-1,4-dihydro-4-oxo-7-(3,5-dimethyl-1-piperazinyl)-3-quinolinecarboxylic acid, 1-cyclopropyl-6-fluoro-1,4-dihydro-4-oxo-7-(3-methyl-1-piperazinyl)-3-quinolinecarboxylic acid, 1-cyclopropyl-6-fluoro-1,4-dihydro-4-oxo-7-(3-ethyl-1-piperazinyl)-3-quinolinecarboxylic acid, 1-cyclopropyl-6-fluoro-1,4-dihydro-4-oxo-7-(3,5-diethyl-1-piperazinyl)-3-quinolinecarboxylic acid, 1-cyclopropyl-6-fluoro-1,4-dihydro-4-oxo-7-(2,3,5-trimethyl-1-piperazinyl)-3-quinolinecarboxylic acid, 1-cyclopropyl-6-fluoro-1,4-dihydro-4-oxo-7-(2,3,5,6-tetramethyl-1-piperazinyl)-3-quinolinecarboxylic acid, 1-cyclopropyl-1,4-dihydro-4-oxo-7-(1-piperazinyl)-3-quinolinecarboxylic acid, 1-cyclopropyl-1,4-dihydro-6-nitro-4-oxo-7-(1-piperazinyl)-3-quinolinecarboxylic acid and 6-chloro-1-cyclopropyl-1,4-dihydro-4-oxo-7-(1-piperazinyl)-3-quinolinecarboxylic acid.

The 7-chloro-1-cyclopropyl-6-fluoro-1,4-dihydro-4-oxo-3-quinolinecarboxylic acid of the formula VIa (VI; X=F) used as an intermediate can be prepared in accordance with the following equation:

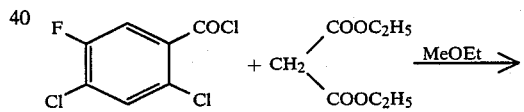

(1)  (2)

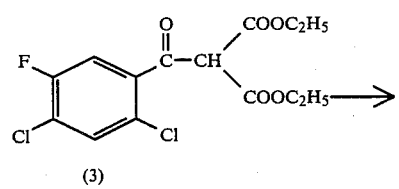

(3)

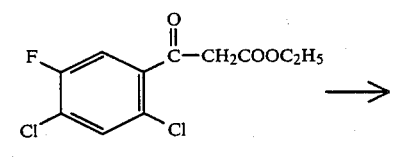

(4)

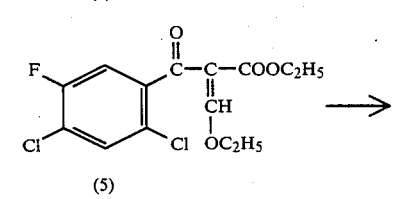

(5)

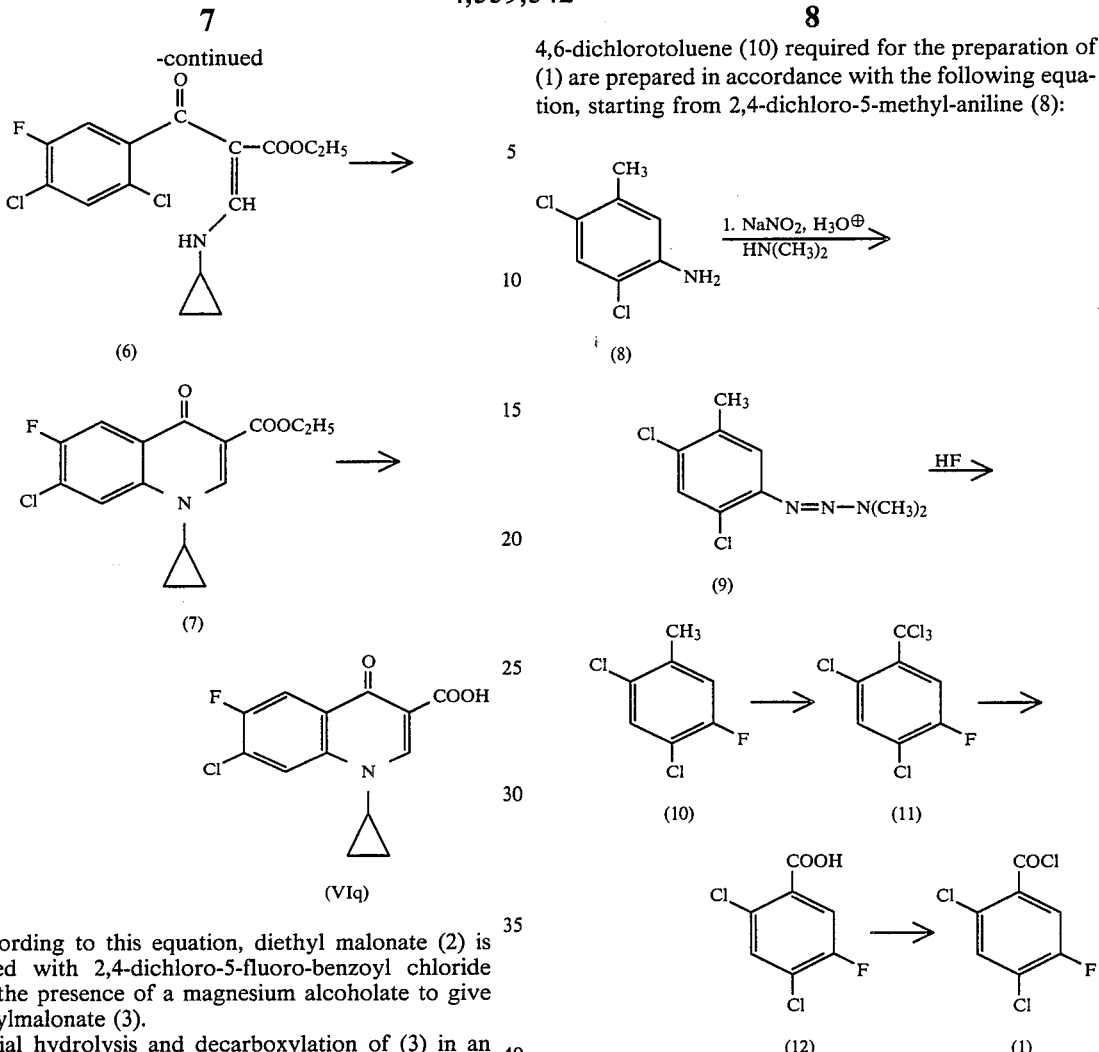

(6)

(7)

(VIq)

According to this equation, diethyl malonate (2) is acylated with 2,4-dichloro-5-fluoro-benzoyl chloride (1) in the presence of a magnesium alcoholate to give the acylmalonate (3).

Partial hydrolysis and decarboxylation of (3) in an aqueous medium with catalytic amounts of p-toluene-sulphonic acid gives a good yield of the ethyl aroylacetate (4), which is converted into the ethyl 2-(2,4-dichloro-5-fluoro-benzoyl)-3-ethoxy-acrylate (5) with o-formic acid triethyl ester/acetic anhdride. The reaction of (5) with cyclopropylamine in a solvent, such as, for example, methylene chloride, alcohol, chloroform, cyclohexane or toluene, leads to the desired intermediate (6) in a slightly exothermic reaction.

The cyclisation reaction (6)→(7) is carried out in a temperature range from about 60° to 280° C., preferably 80° to 180° C.

Diluents which can be used are dioxane, dimethyl-sulphoxide, N-methyl-pyrrolidone, sulpholane, hexamethylphosphoric acid triamide and, preferably, N,N-dimethylformamide.

Possible acid-binding agents for this reaction stage are potassium tert.-butanolate, butyl-lithium, lithiumphenyl, phenyl-magnesium bromide, sodium methylate, sodium hydride and, particularly preferably, potassium carbonate or sodium carbonate. It may be advantageous to employ an excess of 10 mole % of base.

The ester hydrolysis of (7) under basic or acid conditions, which is carried out in the last step, leads to 7-chloro-1-cyclopropyl-6-fluoro-1,4-dihydro-4-oxo-3-quinolinecarboxylic acid VIa.

The 2,4-dichloro-5-fluoro-benzoyl chloride (1) used as the starting material for this synthesis route and the corresponding carboxylic acid, as well as the 3-fluoro-4,6-dichlorotoluene (10) required for the preparation of (1) are prepared in accordance with the following equation, starting from 2,4-dichloro-5-methyl-aniline (8):

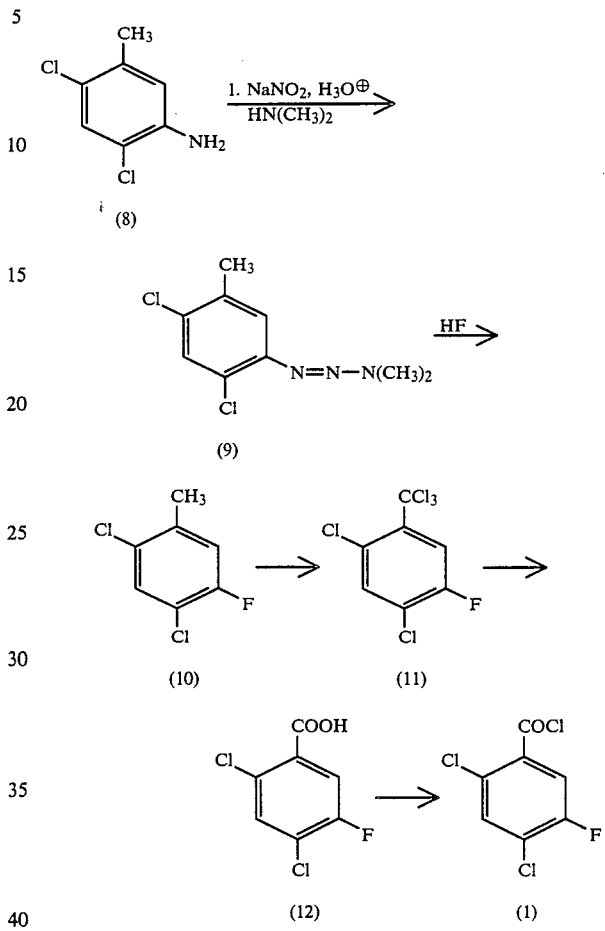

According to this equation, 2,4-dichloro-5-methyl-aniline (8) is diazotised with the aid of NaNO$_2$ and the diazonium salt thereby formed is converted into the triazene (9) with dimethylamine.

The triazene (9) is dissolved in excess anhydrous HF. The triazene thereby splits into 2,4-dichloro-5-methyl-diazonium fluoride and dimethylamine. This solution is split, without intermediate isolation, into 3-fluoro-4,6-dichlorotoluene (10) by the action of heat at 130°–140°, N$_2$ being split off. Yield: 77% of theory.

The 3-fluoro-4,6-dichlorotoluene (10) is chlorinated in a temperature range of 110° to 160° C. under irradiation with UV light, to give 2,4-dichloro-5-fluoro-1-trichloromethylbenzene (11).

Hydrolysis of (11) with 95% strength sulphuric acid leads to 2,4-dichloro-5-fluoro-benzoic acid (12), which is converted into the carboxylic acid chloride (1) (boiling point 121°/20 mbar; n$_D^{20}$ 1.5722) with thionyl chloride.

The following quinolonecarboxylic acids used as intermediates are prepared in an analogous manner: 7-Chloro-1-cyclopropyl-1,4-dihydro-4-oxo-3-quinolinecarboxylic acid (VIb) (melting point 308° C.) from 2,4-dichlorobenzoyl chloride (J. Chem. Soc. 83, 1213 (1903));

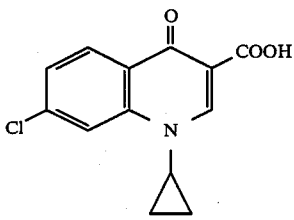

6,7-Dichloro-1-cyclopropyl-1,4-dihydro-4-oxo-3-quinolinecarboxylic acid (VIc) (melting point 265° C.) from 2,4,5-trichlorobenzoyl chloride;

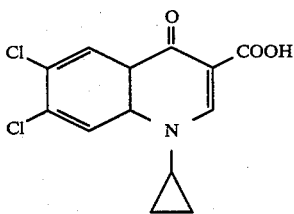

7-Chloro-1-cyclopropyl-1,4-dihydro-6-nitro-4-oxo-3-quinolinecarboxylic acid (VId) (melting point 265° to 275° C., decomposition) from 2,4-dichloro-5-nitro-benzoyl chloride

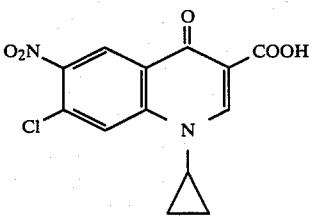

The compounds of the formula (III) which can be used according to the invention are already known, or they can be obtained by known processes. Examples which may be mentioned are: methyl bromoacetate, ethyl bromoacetate, methyl 2-chloropropionate, benzyl 3-iodopropionate, ethyl 4-bromobutyrate, benzyl 6-iodohexanoate, benzyl α-bromophenylacetate, bromoacetic acid, chloroacetamide, N-methyl-chloroacetamide, N-pentylchloroacetamide, chloroacetonitrile, methyl α-chloroacetoacetate, ethyl α-bromoacetoacetate, diethyl bromomalonate, ethyl bromocyanoacetate, bromomalonic acid diamide, bromomalonic acid dinitrile, bromocyanoacetamide, 3-bromo-2-tetrahydrofuranone, dimethyl methoxymethylenemalonate, diethyl ethoxymethylenemalonate, methyl methoxymethyleneacetoacetate, ethoxymethylene-malonic acid dinitrile and methyl methoxymethylene-cyanoacetate.

The compounds of the formula (IV) which can be used according to the invention are known. Examples which may be mentioned are: methyl acrylate, ethyl acrylate, butyl acrylate, hexyl acrylate, benzyl acrylate, methyl methacrylate, acrylonitrile, 2-chloroacrylonitrile, methyl vinyl sulphone and diethyl vinylphosphonate.

The compounds of the formula (V) which can be used according to the invention can be obtained by methods A and B described above.

The reaction of (II) with (III) (method A) is preferably carried out in a diluent, such as dimethylsulphoxide, N,N-dimethylformamide, tetrahydrofuran, sulpholane, dioxane, pyridine or mixtures of these diluents, at temperatures from 0° to 150° C., preferably 30° C. to 110° C.

The reaction can be carried out under normal pressure, but also under increased pressure. In general, it is carried out under pressures between about 1 and about 100 bar, preferably between 1 and 10 bar.

All the customary inorganic and organic acid-binding agents can be used as acid-binders. These include, preferably, the alkali metal hydroxides and alkali metal carbonates, pyridine and tertiary amines, such as triethylamine and 1,4-diazabicyclo[2,2,2]octane. The reaction can be facilitated by addition of potassium iodide.

In carrying out the process according to the invention, 1 to 4 moles, preferably 1 to 1.5 moles, of the compound (III) are employed per mole of the compound (II).

The reaction of (II) with (IV) (method B) is preferably carried out in a diluent, such as dioxane, dimethylsulphoxide, N,N-dimethylformamide, methanol, ethanol, isopropanol, n-propanol or glycol monomethyl ether, or in mixtures of these diluents.

The reaction temperatures can be varied within a substantial range. In general, the reaction is carried out between about 20° C. and about 150° C., preferably between 50° C. and 100° C.

The reaction can be carried out under normal pressure, but also under increased pressure. In general, it is carried out under pressures between about 1 and about 100 bar, preferably between 1 and 10 bar.

In carrying out the process according to the invention, 1–5 moles, preferably 1–2 moles, of the compound (IV) are employed per mole of the compound (II).

The reaction of the compounds (V) to give the dicarboxylic acids (Ib) (method C) is carried out either in alcoholic sodium hydroxide solution or potassium hydroxide solution or under acid conditions in mixtures of sulphuric acid or hydrogen chloride in acetic acid and/or water. The hydrogenolysis of benzyl esters (V; R'=benzyl) can be carried out in acetic acid in the presence of palladium catalysts.

The reaction is in general carried out at temperatures of 20° C. to 160°C., preferably at 30° to 140° C.

The reaction can be carried out under normal pressure, but also under increased pressure. In general, it is carried out under pressures between about 1 and about 100 bar, preferably between 1 and 10 bar.

Specific new antibacterial active compounds which may be mentioned are: 7-[4-(methoxycarbonylmethyl)-1-piperazinyl]-1-cyclopropyl-6-fluoro-1,4-dihydro-4-oxo-3-quinolinecarboxylic acid, 7-[4-(ethoxycarbonylmethyl)-1-piperazinyl]-1-cyclopropyl-6-fluoro-1,4-dihydro-4-oxo-3-quinolinecarboxylic acid, 7-[4-(2-benzyloxycarbonylethyl)-1-piperazinyl]-1-cyclopropyl-6-fluoro-1,4-dihydro-4-oxo-3-quinolinecarboxylic acid, 7-[4-(5-benzyloxycarbonylpentyl)-1-piperazinyl]-1-cyclopropyl-6-fluoro-1,4-dihydro-4-oxo-3-quinolinecarboxylic acid, 7-[4-(2-methoxycarbonylethyl)-1-piperazinyl]-1-cyclopropyl-6-fluoro-1,4-dihydro-4-oxo-3-quinolinecarboxylic acid, 7-[4-(2-ethoxycarbonylethyl)-1-piperazinyl]-1-cyclopropyl-6-fluoro-1,4-dihydro-4-oxo-3-quinolinecarboxylic acid, 7-[4-(2-propyloxycarbonylethyl)-1-piperazinyl]-1-cyclopropyl-6-fluoro-1,4-dihydro-4-oxo-3-quinolinecarboxylic acid, 7-[4-(2-n-butoxycarbonylethyl)-1-piperazinyl]-1-cyclopropyl-6-fluoro-1,4-dihydro-4-oxo-3-quinolinecarboxylic acid, 7-[4-(2-cyanoethyl)-1-piperazinyl]-1-cyclopropyl-6-fluoro-1,4-dihydro-4-oxo-3-quinolinecarboxylic acid, 7-[4-(3-cyanopropyl)-1-piperazinyl]-1-cyclopropyl-6-fluoro-1,4-dihydro-4-oxo-3-quinolinecarboxylic acid, 7-{4-[α-(benzyloxycarbonyl)-benzyl]-1piperazinyl}-1-cyclopropyl-6-fluoro-1,4-dihydro-4-oxo-3-quinolinecarboxylic acid, 7-[4-carbamoylmethyl-1-piperazinyl]-1-cyclopropyl-6-fluoro-1,4-dihydro-4-oxo-3-quinolinecarboxylic acid, 7-[4-cyanomethyl- -1-piperazinyl]-1-cyclopropyl-6-fluoro-1,4-dihydro-4-oxo-3-quinolinecarboxylic acid, 7-[4-(N-methylcarbamoylmethyl)-1-piperazinyl]-1-cyclopropyl-6-fluoro-1,4-dihydro-4-oxo-3-quinolinecarboxylic acid, 7-[4-(N-ethylcarbamoylmethyl)-1-piperazinyl]-1-cyclopropyl-6-fluoro-1,4-dihydro-4-oxo-3-quinolinecarboxylic acid, 7-{4-[2-oxo-1-(methoxycarbonyl)-1-propyl]-1-piperazinyl}-1-cyclopropyl-6-fluoro-1,4-dihydro-4-oxo-3-quinolinecarboxylic acid, 7-[4-(2-oxo-tetrahydrofur-3-yl)-1-piperazinyl]-1-cyclopropyl-6-fluoro-1,4-dihydro-4-oxo-3-quinolinecarboxylic acid, 7-[4-(carboxymethyl)-1-piperazinyl]-1-cyclopropyl-6-fluoro-1,4-dihydro-4-oxo-3-quinolinecarboxylic acid, 7-[4-(2-carboxyethyl)-1-piperazinyl]-1-cyclopropyl-6-fluoro-1,4-dihydro-4-oxo-3-quinolinecarboxylic acid, 7-[4-(2-carboxypropyl)-1-piperazinyl]-1-cyclopropyl-6-fluoro-1,4-dihydro-4-oxo-3-quinolinecarboxylic acid, 7-[4-(3-carboxypropyl)-1-piperazinyl]-1-cyclopropyl-6-fluoro-1,4-dihydro-4-oxo-3-quinolinecarboxylic acid, 7-[4-(5-carboxypentyl)-1-piperazinyl]-1-cyclopropyl-6-fluoro-1,4-dihydro-4-oxo-3-quinolinecarboxylic acid, 7-[4(α-carboxybenzyl)-1-piperazinyl]-1-cyclopropyl-6-fluoro-1,4-dihydro-4-oxo-3-quinolinecarboxylic acid, 7-[4-(2-chloro-2-cyanoethyl)-1-piperazinyl]-1-cyclopropyl-6-fluoro-1,4-dihydro-4-oxo-3-quinolinecarboxylic acid, 7-[4-(2-methylsulphonyl-ethyl)-1-piperazinyl]-1-cyclopropyl-6-fluoro-1,4-dihydro-4-oxo-3-quinolinecarboxylic acid, 7-[4-(2-diethoxyphosphonylethyl)-1-piperazinyl]-1-cyclopropyl-6-fluoro-1,4-dihydro-4-oxo-3-quinolinecarboxylic acid, 7-[4-(2-methoxycarbonylethyl)-1-piperazinyl]-1-cyclopropyl-1,4-dihydro-6-nitro-4-oxo-3-quinolinecarboxylic acid, 7-[4-(2-methoxycarbonylethyl)-1-piperazinyl]-6-chloro-1-cyclopropyl-1,4-dihydro-4-oxo-3-quinolinecarboxylic acid, 7-[4-(2-methoxycarbonylethyl)-1-piperazinyl]-1-cyclopropyl-1,4-dihydro-4-oxo-3-quinolinecarboxylic acid, 7-[4-(2-benzyloxycarbonylethyl)-3-methyl-1-piperazinyl]-1-cyclopropyl-6-fluoro-1,4-dihydro- 4-oxo-3-quinolinecarboxylic acid and 7-[4-(2-methoxycarbonylethyl)-3,5-dimethyl-1-piperazinyl]-1-cyclopropyl-6-fluoro-1,4-dihydro-4-oxo-3-quinolinecarboxylic acid.

If desired, the compounds of the formula (I) according to the invention can be converted into a salt with an organic or inorganic acid. Examples of acids which are suitable for salt formation are the hydrogen halide acids, such as hydrochloric acid, hydrobromic acid and hydriodic acid, sulphuric acid, acetic acid, citric acid, ascorbic acid and benzenesulphonic acid. Preferred suitable alkali metal salts and alkaline earth metal salts are the sodium, potassium, calcium and magnesium salts.

Preparation examples for the starting compounds:

EXAMPLE A

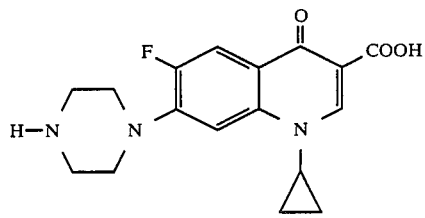

A mixture of 19.7 g of 7-chloro-1-cyclopropyl-6-fluoro-1,4-dihydro-4-oxo-3-quinolinecarboxylic acid, 30.1 g of anhydrous piperazine and 100 ml of dimethylsulphoxide is heated at 135° to 140° C. for 2 hours. The solvent is distilled off under a fine vacuum and the residue is suspended in H₂O, filtered off with suction and washed with water. For further purification, the moist crude product is boiled up with 100 ml of water, filtered off with suction at room temperature, washed with H₂O and dried to constant weight over CaCl₂ at 100° C. in a vacuum drying cabinet. 19.6 g of 1-cyclopropyl-6-fluoro-1,4-dihydro-4-oxo-7-(1-piperazinyl)-3-quinolinecarboxylic acid of decomposition point 255° to 257° C. are obtained.

The 7-chloro-1-cyclopropyl-6-fluoro-1,4-dihydro-4-oxo-3-quinolinecarboxylic acid VIa used as the starting material is prepared as follows:

24.3 g of magnesium filings are suspended in 50 ml of anhydrous ethanol. 5 ml of carbon tetrachloride are added and, when the reaction has started, a mixture of 160 g of diethyl malonate, 100 ml of absolute ethanol and 400 ml of anhydrous ether is added dropwise, whereupon vigorous reflux can be observed. When the reaction has subsided, the mixture is heated at the boiling point for a further 2 hours and cooled to −5° C. to −10° C. with dry ice/acetone, and a solution of 227.5 g of 2,4-dichloro-5-fluorobenzoyl chloride (1) in 100 ml of absolute ether is slowly added dropwise at this temperature. The mixture is stirred at 0° C. to −5° C. for 1 hour and allowed to come to room temperature overnight, and a mixture of 400 ml of ice-water and 25 ml of concentrated sulphuric acid is allowed to run in, while cooling with ice. The phases are separated and subsequently extracted twice with ether. The combined ether solutions are washed with saturated NaCl solution and dried with Na₂SO₄ and the solvent is stripped off in vacuo. 349.5 g of diethyl 2,4-dichloro-5-fluoro-benzoylmalonate (3) are obtained as the crude product.

0.15 g of p-toluenesulphonic acid is added to an emulsion of 34.9 g of crude diethyl 2,4-dichloro-5-fluorobenzoylmalonate (3) in 50 ml of water. The mixture is heated at the boiling point for 3 hours, while stirring thoroughly, the cooled emulsion is extracted several times with methylene chloride, the combined CH₂Cl₂ solutions are washed once with saturated NaCl solution and dried with Na₂SO₄ and the solvent is distilled off in vacuo. Fractionation of the residue in vacuo gives 21.8 g of ethyl 2,4-dichloro-5-fluoro-benzoylacetate (4) of boiling point 127° to 142° C./0.09 mbar.

A mixture of 21.1 g of ethyl 2,4-dichloro-5- fluorobenzoyl-acetate (4), 16.65 g of ethyl o-formate and 18.55 g of acetic anhydride is heated at 150° C. for 2 hours. The volatile constituents are then distilled off under a waterpump vacuum and finally under a fine vacuum at a bath temperature of 120° C. 25.2 g of crude ethyl 2-(2,4-dichloro-5-benzoyl)-3-ethoxy-acrylate (5) remain. The product is sufficiently pure for the further reactions.

4.3 g of cyclopropylamine are added dropwise to a solution of 24.9 g of ethyl 2-(2,4-dichloro-5-fluorobenzoyl)-3-ethoxy-acrylate (5) in 80 ml of ethanol, while cooling with ice and stirring. When the exothermic reaction has subsided, the mixture is stirred for a further hour at room temperature, the solvent is stripped off in vacuo and the residue is recrystallised from cyclohexane/petroleum ether. 22.9 g of ethyl 2-(2,4-dichloro-5-fluoro-benzoyl)-3-cyclopropylamino-acrylate (6) of melting point 89° to 90° C. are obtained.

3.44 g of 80% pure sodium hydride are added in portions to a solution of 31.9 g of ethyl 2-(2,4-dichloro-5-fluoro-benzoyl)-3-cyclopropylamino-acrylate (6) in 100 ml of anhydrous dioxane, while cooling with ice and stirring. The mixture is then stirred at room temperature for 30 minutes and under reflux for 2 hours and the dioxane is stripped off in vacuo. The residue (40.3 g) is suspended in 150 ml of water, 6.65 g of potassium hydroxide are added and the mixture is refluxed for 1.5 hours. The warm solution is filtered and the residue is rinsed with $H_2O$. The filtrate is then acidified to pH 1–2 with half-concentrated hydrochloric acid, while cooling with ice, and the precipitate is filtered off with suction, washed with water and dried in vacuo at 100° C. 27.7 g of 7-chloro-1-cyclopropyl-6-fluoro-1,4-dihydro-4-oxo-3-quinolinecarboxylic acid VIa of melting point 234° to 237° C. are obtained in this manner.

EXAMPLE B

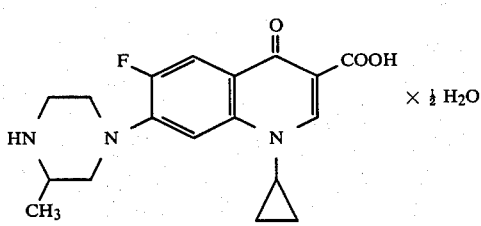

A mixture of 2.8 g (0.01 mole) of 7-chloro-1-cyclopropyl-6-fluoro-1,4-dihydro-4-oxo-3-quinolinecarboxylic acid and 5.1 g (0.051 mole) of 2-methylpiperazine in 6 ml of dimethylsulphoxide is heated at 140° C. for 2 hours. The solvent is then distilled off under a high vacuum, 6 ml of hot water are added to the residue and the mixture is kept at 95° C. for 1 hour. It is cooled with ice and the precipitate which has separated out is filtered off with suction, washed with a little water and dissolved in a mixture of 0.8 ml of acetic acid and 10 ml of water at 90° to 100° C. The filtrate is brought to pH 8 with potassium hydroxide solution (0.75 g of KOH in 0.7 ml of water) and the precipitate which has separated out is recrystallised from methanol. 1.8 g (52% of theory) of 1-cyclopropyl-6-fluoro-1,4-dihydro-4-oxo-7-(3-methyl-1-piperazinyl)-3-quinolinecarboxylic acid semihydrate of decomposition point 230° to 232° C. are obtained.

EXAMPLE C

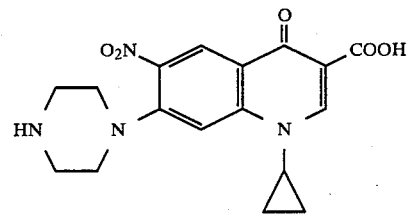

A mixture of 9.3 g (0.03 mole) of 7-chloro-1-cyclopropyl-1,4-dihydro-6-nitro-4-oxo-3-quinolinecarboxylic acid and 12.9 g (0.15 mole) of piperazine is warmed to 120° C. in 60 ml of dimethylsulphoxide for 15 minutes. After a short time, a precipitate separates out of the hot solution. The mixture is concentrated under a high vacuum, the residue is stirred with 30 ml of water and the mixture is heated again to 95° C. for 30 minutes. The mixture is adjusted to pH 8 with 2N hydrochloric acid and the precipitate is filtered off with suction and washed with water and methanol. 5.8 g (54% of theory) of 1-cyclopropyl-1,4-dihydro-6-nitro-4-oxo-7-(1-piperazinyl)-3-quinolinecarboxylic acid of decomposition point 296° to 298° C. are isolated.

EXAMPLE D

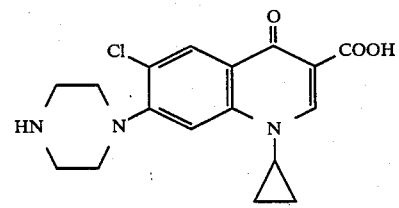

6,7-Dichloro-1-cyclopropyl-1,4-dihydro-4-oxo-3-quinolinecarboxylic acid is reacted analogously to Example C to give 1-cyclopropyl-6-chloro-1,4-dihydro-4-oxo-7-(1-piperazinyl)-3-quinolinecarboxylic acid of decomposition point 295° to 298° C.

EXAMPLE E

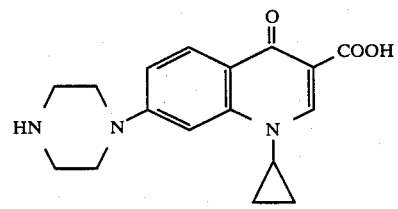

7-Chloro-1-cyclopropyl-1,4-dihydro-4-oxo-3-quinolinecarboxylic acid is reacted with piperazine analogously to Example C to give 1-cyclopropyl-1,4-dihydro-4-oxo-7-(1-piperazinyl)-3-quinolinecarboxylic acid of decomposition point 298° to 300° C.

Preparation examples for the end products according to the invention:

EXAMPLE 1

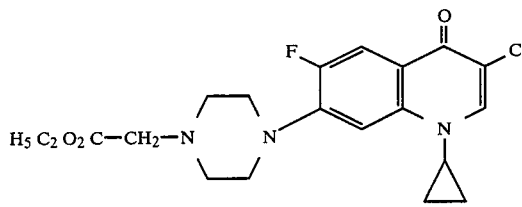

3.3 g (0.01 mole) of 1-cyclopropyl-6-fluoro-1,4-dihydro-4-oxo-7-(1-piperazinyl)-3-quinolinecarboxylic acid in 50 ml of dimethylformamide are heated at 90° C. with 2.5 g (0.015 mole) of ethyl bromoacetate, 2.1 g (0.02 mole) of triethylamine and 2.5 g of potassium iodide for 5 hours. The reaction mixture is poured into 30 ml of water and the precipitate is filtered off with suction, washed with water and recrystallised from methanol. 2.5 g of 1-cyclopropyl-6-fluoro-7-[4-ethoxycarbonylmethyl)-1-piperazinyl]-1,4-dihydro-4-oxo-3-quinolinecarboxylic acid of melting point 192° to 194° C. are obtained.

The following compounds are obtained analogously to Example 1:

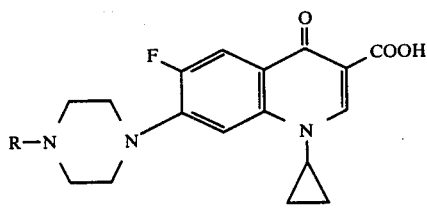

| Example | R | Melting point (°C.) |
|---|---|---|
| 2 | C6H5CH2O—CO—CH—<br>                              \|<br>                              C6H5 | 170 (decomposition) |
| 3 | H2N—CO—CH2— | 254 (decomposition) |
| 4 | NC—CH2— | 166 (decomposition) |

EXAMPLE 5

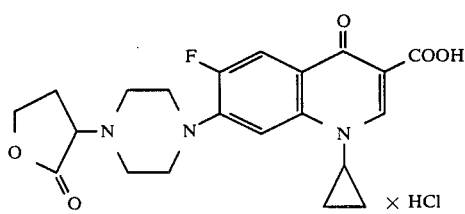

The procedure followed is analogous to Example 1, with α-bromobutyrolactone as the alkylating agent. The reaction product is treated with dilute hydrochloric acid to give 1-cyclopropyl-6-fluoro-1,4-dihydro-4-oxo-7-[4-(2-oxo-tetrahydrofur-3-yl)-1-piperazinyl]-3-quinolinecarboxylic acid hydrochloride of decomposition point 270° C.

Mass spectrum: m/e 415 (M+), 371, 342, 331, 301, 298, 289, 287, 275, 257, 245, 229 and 36 (100%, HCL).

EXAMPLE 6

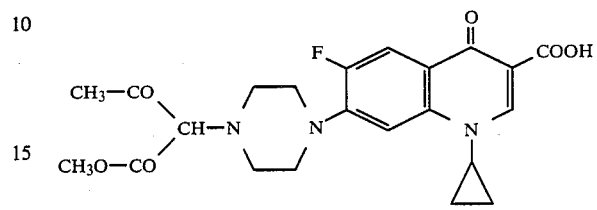

6.6 g (0.02 mole) of 1-cyclopropyl-6-fluoro-1,4-dihydro-4-oxo-7-(1-piperazinyl)-3-quinolinecarboxylic acid are heated at 80° C. with 4.5 g of methyl 2-chloroacetoacetate and 4.2 g of triethylamine in 100 ml of dimethylformamide for 3 hours. The solution is then concentrated in vacuo, the residue is stirred with 50 ml of water and the resulting solid product is washed with water and methanol and recrystallised from glycol monomethyl ether. 3.9 g (44% of theory) of 1-cyclopropyl-6-fluoro-1,4-dihydro-4-oxo-7-{4-[2-oxo-1-(methoxycarbonyl)-1-propyl]-1-piperazinyl}-3-quinolinecarboxylic acid of decomposition point 224° to 228° C. are isolated.

EXAMPLE 7

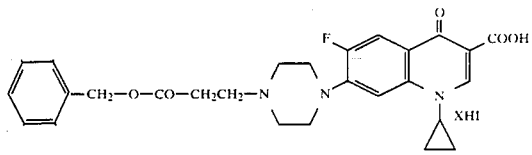

3.3 g (0.01 mole) of 1-cyclopropyl-6-fluoro-1,4-dihydro-4-oxo-7-(1-piperazinyl)-3-quinolinecarboxylic acid in 50 ml of dimethylformamide are heated at 70° to 80° C. with 5.8 g of benzyl 3-iodopropionate and 2.1 g of triethylamine for 2½ hours, while stirring. The solution is concentrated in vacuo, 30 ml of water are added to the residue and the pH is adjusted to 5. The precipitate is filtered off with suction and boiled up with methanol, whereupon 2.8 g of 7-[4-(2-benzyloxycarbonylethyl)-1-piperazinyl]-1-cyclopropyl-6-fluoro-1,4-dihydro-4-oxo-3-quinolinecarboxylic acid hydriodide of decomposition point 206° to 210° C. are obtained.

The benzyl 3-iodopropionate used as the starting substance is obtained as follows:

99 g of benzyl 3-chloropropionate are heated under reflux with 90 g of sodium iodide in 460 ml of acetone for 1 day. The reaction mixture is concentrated, 200 ml of methylene chloride are added and the mixture is washed with 3×100 ml of water. After drying with sodium sulphate, the mixture is concentrated and the residue is distilled under a high vacuum; yield: 91 g of benzyl 3-iodopropionate of boiling point 105° to 108° C./0.1 mmHg.

EXAMPLE 8

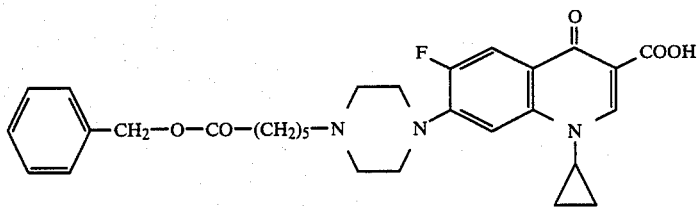

The procedure followed is analogous to Example 7, using benzyl 6-iodohexanoate, and 7-[4-(5-benzyloxycarbonylpentyl)-1-piperazinyl]-1-cyclopropyl-6-fluoro-1,4-dihydro-4-oxo-3-quinolinecarboxylic acid of melting point 176° to 178° C. is obtained.

The benzyl 6-iodohexanoate used as the starting substance is obtained as follows:

46.5 g (0.3 mole) of 6-chlorohexanoic acid and 35.6 g of benzyl alcohol are heated in 500 ml of toluene in the presence of 1 g of p-toluenesulphonic acid, using a water separator. When the reaction has ended, the mixture is washed with 5% strength sodium bicarbonate solution and water, dried with sodium sulphate and concentrated and the residue is distilled, whereupon 61.5 g (85% of theory) of benzyl 6-chlorohexanoate of boiling point 163° to 165° C./4 mm Hg are obtained.

60 g (0.25 mole) of benzyl 6-chlorohexanoate are heated under reflux with 45 g of sodium iodide in 230 ml of acetone for 5 hours. The suspension is concentrated, 300 ml of methylene chloride are added and the mixture is washed with 2×200 ml of water. The organic phase is dried with sodium sulphate and concentrated and the residue is distilled in a bulb tube distillation apparatus. 63.8 g (77% of theory) of benzyl 6-iodohexanoate pass over at 220° to 230° C. (oven temperature)/0.4 mm Hg.

EXAMPLE 9

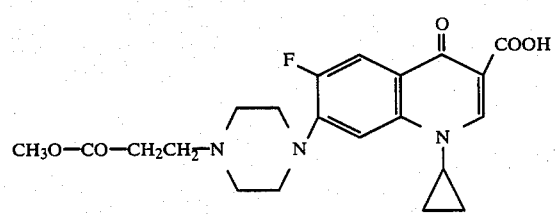

A mixture of 3.31 g (0.01 mole) of 1-cyclopropyl-6-fluoro-1,4-dihydro-4-oxo-7-(1-piperazinyl)-3-quinolinecarboxylic acid and 5 g (0.058 mole) of methyl acrylate in 50 ml of ethanol is heated under reflux for 2 hours. The solution is poured into 10 ml of water and the precipitate is filtered off with suction, washed with methanol and recrystallised from glycol monomethyl ether. 2.9 g (70% of theory) of 1-cyclopropyl-6-fluoro-1,4-dihydro-4-oxo-7-[4-(2-methoxycarbonylethyl)-1-piperazinyl]-3-quinolinecarboxylic acid of decomposition point 192° to 194° C. are obtained.

The following compounds are obtained analogously to Example 9:

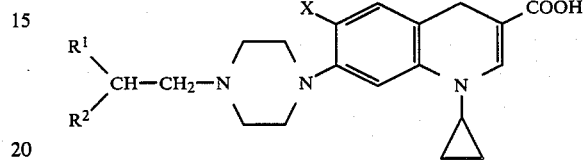

| Example | R¹ | R² | X | Melting point (°C.) |
|---------|-----|-----|----|---------------------|
| 10 | C₂H₅O—CO | H | F | 142 (decomposition) |
| 11 | C₄H₉O—CO | H | F | 141 (decomposition) |
| 12 | C₆H₅CH₂O—CO | H | F | 140 |
| 13 | CH₃O—CO | H | Cl | 183 |
| 14 | CN | H | F | 255 (decomposition)+ |
| 15 | CN | Cl | F | 202 (decomposition)++ |
| 16 | CH₃—SO₂ | H | F | 258 (decomposition) |

+According to the ¹H nuclear magnetic resonance spectrum, the 7-[4-(2-cyanoethyl)-1-piperazinyl]-1-cyclopropyl-6-fluoro-1,4-dihydro-4-oxo-3-quinoline-carboxylic acid is present as a mixture with ~15% of 7-[4-(1-cyanoethyl)-1-piperazinyl]-1-cyclopropyl-6-fluoro-1,4-dihydro-4-oxo-3-quinolinecarboxylic acid.
++Mass spectrum: m/e 382 (M⁺-HCl), 338 (382-CO₂), 331, 289, 287, 245, 218, 154, 152, 44 (CO₂) and 36 (100%, HCl).

EXAMPLE 17

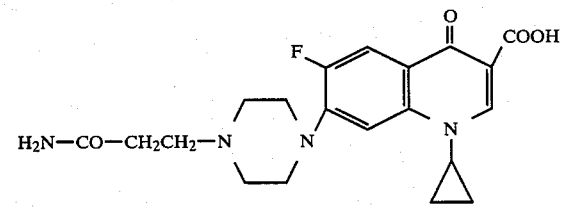

A mixture of 3.31 g (0.01 mole) of 1-cyclopropyl-6-fluoro-1,4-dihydro-4-oxo-7-(1-piperazinyl)-3-quinolinecarboxylic acid and 4.2 g (0.058 mole) of acrylamide in 50 ml of dimethylformamide is heated at 140° C. for 6 hours. The suspension is concentrated under a high vacuum and the residue is stirred with water and recrystallised from glycol monomethyl ether. 2 g (50% of theory) of 7-[4-(2-carbamoylethyl)-1-piperazinyl]-1-cyclopropyl-6-fluoro-1,4-dihydro-4-oxo-3-quinolinecarboxylic acid of decomposition point 283° to 286° C. are obtained.

EXAMPLE 18

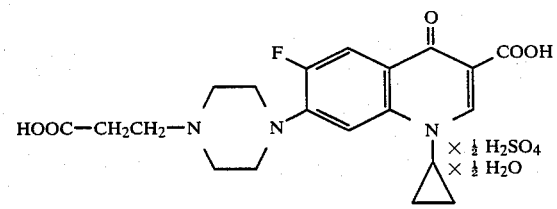

2.9 g of the compound of Example 9 are dissolved in a mixture of 14 ml of acetic acid and 9.5 ml of water, and 1.4 ml of concentrated sulphuric acid are added. The mixture is heated at 150° to 160° C. for 1.5 hours and poured into 90 ml of water. The precipitate is filtered off with suction, washed with water and methanol and dried. 2.3 g (72% of theory) of 7-]4-(2carboxyethyl)-1-piperazinyl]-1-cyclopropyl-6-fluoro-1,4-dihydro-4-oxo-3-quinolinecarboxylic acid semisulphate semihydrate of decomposition point 258° to 261° C. are isolated.

$C_{20}H_{22}FN_3O_5$. ½ $H_2SO_4$. ½ $H_2O$ (461.4): calculated: C:52.06, H:5.24, N:9.11, S:3.47; found: C:51.7, H:5.3, N:9.1, S:3.9.

The following compounds are obtained analogously to Example 12:

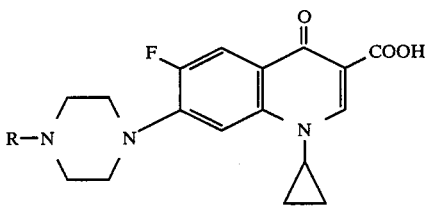

| Example | R | Melting point (°C.) |
|---|---|---|
| 19 | HOOC—$CH_2$— × 2½ $H_2O$ | 276 (decomposition)[1] |
| 20 | HOOC—$(CH_2)_5$— × ½ $H_2SO_4$ × ½ $H_2O$ | 254 (decomposition) |
| 21 | HOOC—CH— × $H_2O$<br>      \|<br>      $C_6H_5$ | 214 (decomposition)[2] |

[1] The reaction product (as the sulphate) was dissolved in dilute sodium hydroxide solution and precipitated as the betaine at pH 5 with dilute hydrochloric acid.
[2] The reaction mixture is poured onto water and adjusted to pH 4 with dilute sodium hydroxide solution and the betaine is isolated.

EXAMPLE 22

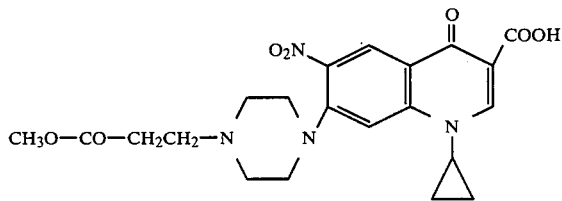

537 mg (1.5 mmol) of 1-cyclopropyl-1,4-dihydro-6-nitro-4-oxo-7-(1-piperazinyl)-3-quinolinecarboxylic acid are heated under reflux in a mixture of 7.5 ml of glycol monomethyl ether and 3 ml of dimethylsulphoxide with 2 g of methyl acrylate for 8 hours. 10 ml of water are added to the solution and the precipitate is filtered off with suction, washed with methanol and dried. 0.5 g of 1-cyclopropyl-1,4-dihydro-7-[4-(2-ethoxycarbonylethyl)-1-piperazinyl]-6-nitro-4-oxo-3-quinolinecarboxylic acid of decomposition point 208° to 211° C. is obtained.

EXAMPLE 23

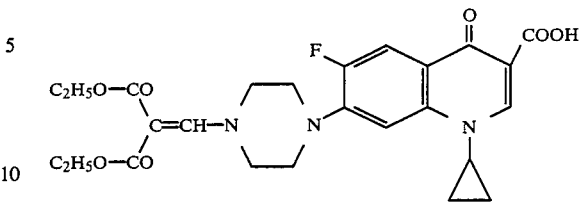

3.3 g of 1-cyclopropyl-6-fluoro-1,4-dihydro-4-oxo-7-(1-piperazinyl)-3-quinolinecarboxylic acid are stirred with 2.8 g of diethyl ethoxymethylenemalonate in a mixture of 0.4 g of sodium hydroxide in 5 ml of water and 25 ml of dioxane at room temperature for 5 hours. The mixture is left to stand overnight, the small amount of undissolved material is filtered off and the filtrate is concentrated. The residue is taken up in about 30 ml of water, the pH is adjusted to 4 with dilute hydrochloric acid and the precipitate which has separated out is immediately filtered off with suction and washed with water. A greasy product which solidifies when stirred with isopropanol is obtained.

Yield: 2.4 g (48% of theory) of 1-cyclopropyl-7-[4-(2,2-diethoxycarbonyl-vinylene)-1-piperazinyl]-6-fluoro-1,4-dihydro-4-oxo-3-quinolinecarboxylic acid of decomposition point 184° to 188° C.

EXAMPLE 24

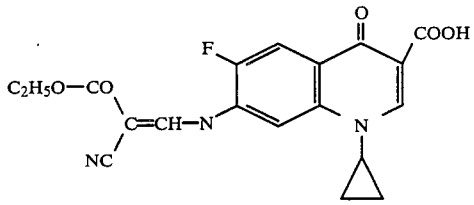

The procedure followed is analogous to Example 23, but with 2.2 g of ethyl ethoxymethylenecyanoacetate, and 2.35 g of 1-cyclopropyl-7-[3-(2-cyano-2-ethoxycarbonylvinylene)-1-piperazinyl]-6-fluoro-1,4-dihydro-4-oxo-3-quinolinecarboxylic acid of decomposition point 245° to 255° C. are obtained.

EXAMPLE 25

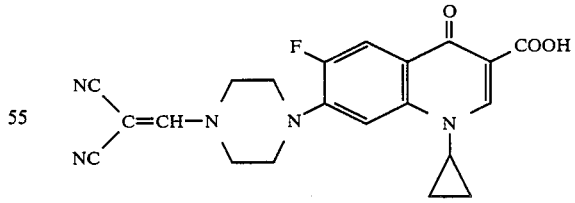

The procedure followed is analogous to Example 23, but with 1.6 g of ethoxymethylenemalonic acid dinitrile, and 4 g of 1-cyclopropyl-7-[4-(2,2-dicyano-vinylene)-1-piperazinyl]-6-fluoro-1,4-dihydro-4-oxo-3-quinolinecarboxylic acid are obtained as a sparingly soluble product, which is washed with methanol; decomposition point 275° to 283° C.

Mass spectrum: m/e=363 ($M^+$—$CO_2$), 362 ($M^+$—COOH), 315, 287, 245 and 44 (100%, $CO_2$).

EXAMPLE 26

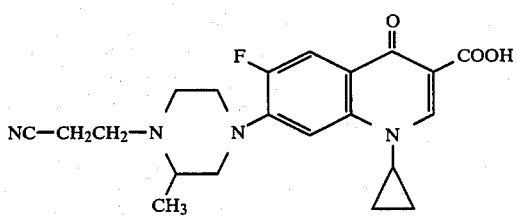

3.45 g of 1-cyclopropyl-6-fluoro-1,4-dihydro-4-oxo-7-(3-methyl-1-piperazinyl)-3-quinolinecarboxylic acid (Example B) are reacted with 4.5 g of acrylonitrile analogously to Example 9, and 3 g of 7-[4-(2-cyanoethyl)-3-methyl-1-piperazinyl]-1-cyclopropyl-6-fluoro-1,4-dihydro-4-oxo-3-quinolinecarboxylic acid of melting point 203°–206° C. are obtained.

$C_{21}H_{23}FN_4O_3$ (398.4): calculated: C:63.3, H:5.8, N:14.1; found: C:63.0, H:5.9, N:13.8.

The compounds according to the invention have good actions against Gram-positive and Gram-negative bacteria, particularly against enterobacteriaceae; in particular even against those which are resistant to a variety of antibiotics, such as, for example; penicillins, cephalosporins, aminoglycosides, sulphonamides and tetracyclins.

The table which follows shows the minimum inhibitory concentrations for compounds according to the invention on some bacteria. They were obtained in an agar dilution test with the aid of Multipoint Inokulator (Denley) on Isosensitest agar.

| Strain | Example 6 | Example 15 |
| --- | --- | --- |
| E. coli Neumann | ≦0.015 | ≦0.015 |
| Klebsiella 8085 | ≦0.015 | ≦0.015 |
| Proteus 1017 | ≦0.015 | ≦0.015 |
| Staph. 133 | 1 | 0.5 |
| Pseudom. Walther | 0.5 | 0.5 |

The compounds according to the invention have low toxicity and a potent and broad antimicrobial efficacy. These properties make it possible to use them as chemotherapeutic active compounds in medicine and as substances for preserving inorganic and organic materials, in particular organic materials of all types, for example polymers, lubricants, dyes, fibres, leather, paper and wood, foodstuffs and water.

The compounds according to the invention are active against a very broad spectrum of microorganisms. Using them, Gram-negative and Gram-positive bacteria and bacterioid microorganisms can be controlled and the diseases caused by these pathogens can be treated.

The compounds according to the invention are particularly active against bacteria and bacterioid microorganisms. Thus they are particularly well suited for the chemotherapy of local and systemic infections caused by these pathogens in medicine.

For example, local and/or systemic diseases caused by the following pathogens or by mixtures of the following pathogens can be treated and/or prevented: Micrococcaceae, such as staphylococci, for example *Staphylococcus aureus, Staph. Epidermidis,* (Staph.=Staphylococcus); Lactobacteriaceae, such as streptococci, for example *Streptococcus pyogenes,* α- and β-haemolytic streptococci, non (γ-) haemolytic streptococci, enterococci and *Diplococcus pneumoniae (pneumococci)* (Str.=Streptococcus); Enterobacteriaceae, such as escherichiae bacteria of the *coli* group: escherichia bacteria, for example *Escherichia coli,* enterobacter bacteria, for example aerogenes, *E. cloacae,* Klebsiella bacteria, for example *K. pneumoniae,* serratia, for example *Serratia marcescens* (E.=Enterobacter) (K.=Klebsiella), proteae bacteria of the proteus groups: proteus, for example *Proteus vulgaris, Pr. morganii, Pr. rettgeri* and *Pr. mirabilis* (Pr.=Proteus); pseudomonadaceae, such as pseudomonas bacteria, for example *Pseudomonas aeruginosa* (PS.=Pseudomonas); bacteroidaceae, such as bacteroides bacteria, for example *Bacteroides fragilis* (B.=Bacteroides); mycoplasma, for example *Mycoplasma pneumonia.*

The above list of pathogens is merely exemplary and should not by any means be interpreted as restrictive.

The following may be mentioned as examples of illness which can be treated by the compounds according to the invention: diseases of the respiratory tract and the pharyngeal cavity: otitis; pharyngitis; pneumonia; peritonitis; pyelonephritis; cystitis; endocarditis; systemic infections; bronchitis; arthritis; local infections and septic diseases.

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar-agar, calcium carbonate and sodium carbonate, (e) solution retarders, for example paraffin, and (f) absorption accelerators, for example quaternary ammonium compound (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminium metahydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutical active compounds in addition to the active compounds according to the invention.

The abovementioned pharmaceutical preparations are manufactured in the usual manner according to known methods, for example by mixing the active compound or the active compounds with the excipient or excipients.

The active compounds or the pharmaceutical preparations can be administered locally, orally, parenterally, intraperitoneally and/or rectally, preferably orally or parenterally, such as intravenously or intramuscularly.

In general, it has proved advantageous in medicine to administer the active compound or compounds in total amounts of about 0.5 to about 50, preferably 1 to 30, especially preferably 1–20 mg/kg of body weight, orally or parenterally, every 24 hours, optionally in the form of several individual administrations, in order to achieve the desired results. An individual administration contains the active compound or the active compounds preferably in amounts of about 1 to about 250, especially of 3 to 60, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be decided by anyone skilled in the art, on the basis of his expert knowledge.

The new compounds can be utilized as feedstuff.

The preparation examples which follow illustrate the invention:

EXAMPLE A (Preparation of the starting material II)

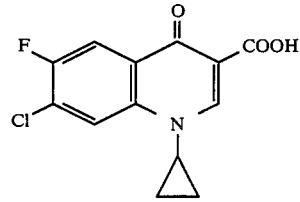

24.3 g of magnesium turnings are suspended in 50 ml of anhydrous ethanol. 5 ml of carbon tetrachloride are added and, when the reaction has started up, a mixture of 160 g of diethyl malonate, 100 ml of absolute ethanol and 400 ml of anhydrous ether is added dropwise, vigorous reflux being observed. After the reaction has moderated, the mixture is heated to boiling for 2 hours, then cooled down to −5° C. to −10° C. with dry ice-/acetone and, at this temperature, a solution of 227.5 g of 2,4-dichloro-5-fluorobenzoyl chloride (1) in 100 ml of absolute ether is slowly added dropwise. The mixture is stirred at 0° to −5° C. for 1 hour, allowed to reach room temperature overnight and, while cooling in ice, a mixture of 400 ml of ice-water and 25 ml of concentrated sulphuric acid is allowed to run in. The phases are separated and the aqueous phase is extracted twice more with ether. The combined ether solutions are washed with saturated NaCl solution, dried with $Na_2SO_4$ and the solvent is removed in vacuo. 349.5 g of diethyl 2,4-dichloro-5-fluorobenzoylmalonate (3) are obtained as a reaction product.

What is claimed is:

1. A quinolonecarboxylic acid of the formula (I),

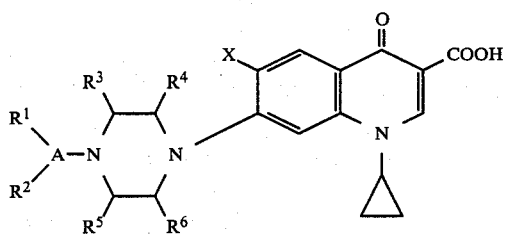

in which
- A denotes straight-chain or branched alkylene with 1 to 5 C atoms or >C=CH—,
- $R^1$ denotes alkoxycarbonyl with 1 to 5 C atoms in the alkyl part, benzyloxycarbonyl, carboxyl, carbamoyl which is optionally substituted by 1 or 2 methyl or ethyl radicals, cyano, methylsulphonyl or ethylsulphonyl and
- $R^2$ denotes hydrogen, alkoxycarbonyl with 1 to 5 C atoms in the alkyl part, benzyloxycarbonyl, carbamoyl, cyano, chlorine, acetyl, alkyl with 1 or 2 carbon atoms or phenyl, or
- $R^1$ and $R^2$, together with the C atom which they substitute, can also form a 2-oxo-tetrahydrofuryl ring,
- $R^3$, $R^4$, $R^5$ and $R^6$ denote hydrogen, methyl or ethyl and
- X denotes hydrogen, fluorine or nitro, and a pharmaceutically useful acid addition, alkali metal or alkaline earth metal salt/s or hydrate thereof.

2. A quinolonecarboxylic acid of the formula (I) in claim 1, in which
- A denotes straight-chain alkylene with 1 to 5 C atoms or >C=CH—,
- $R^1$ denotes alkoxycarbonyl with 1 to 4 C atoms in the alkyl part, benzyloxycarbonyl, carboxyl, carbamoyl, cyano or methylsulphonyl and
- $R^2$ denotes hydrogen, alkoxycarbonyl with 1 to 3 C atoms in the alkyl part, cyano, chlorine, acetyl or phenyl, or
- $R^1$ and $R^2$, together with the C atom which they substitute, can also form a 2-oxo-tetrahydro-3-furyl ring,
- $R^3$ denotes hydrogen, methyl or ethyl,
- $R^4$ denotes hydrogen,
- $R^5$ denotes hydrogen or methyl,
- $R^6$ denotes hydrogen and
- X denotes hydrogen, fluorine, chlorine or nitro.

3. A quinolonecarboxylic acid of the formula (I) in claim 1 which is 1-cyclopropyl-6-fluoro-1,4-dihydro-4-oxo-7-{4-[2-oxo-1-(methoxycarbonyl)-1-propyl]-1-piperazinyl}-3-quinolinecarboxylic acid.

4. A quinolonecarboxylic acid of the formula (I) in claim 1 which is 7-[4-(2-chloro-2-cyano-ethyl)-1-piperazinyl]-1-cyclopropyl-6-fluoro-1,4-dihydro-4-oxo-3-quinolinecarboxylic acid.

5. A quinolonecarboxylic acid of the formula (I) in claim 1 which is 7-[4-(2-benzyloxycarbonyl-ethyl)-1-piperazinyl]-1-cyclopropyl-6-fluoro-1,4-dihydro-4-oxo-3-quinolinecarboxylic acid.

6. A quinolonecarboxylic acid of the formula (I) in claim 1 which is 1-cyclopropyl-6-fluoro-1,4-dihydro-4-oxo-7-[4-(2-methoxycarbonylethyl)-1-piperazinyl]-3-quinolinecarboxylic acid.

7. A quinolonecarboxylic acid of the formula (I) in claim 1 which is 7-[4-cyano-1-piperazinyl]-1-cyclopropyl-6-fluoro-1,4-dihydro-4-oxo-3-quinolinecarboxylic acid.

8. A quinolonecarboxylic acid of the formula (I) in claim 1 which is 7-[4-(2-cyanoethyl)-3-methyl-1-piperazinyl]-1-cyclopropyl-6-fluoro-1,4-dihydro-4-oxo-3-quinolinecarboxylic acid.

9. A pharmaceutical composition containing, as an active ingredient, an antibacterially effective amount of a compound according to claim 1 in admixture with an inert pharmaceutical carrier.

10. A pharmaceutical composition containing, as an active ingredient, an antibacterially effective amount of a compound according to claim 1 in the form of sterile or physiologically isotonic aqueous solution.

11. A composition according to claim 9 containing from 0.5 to 90% by weight of the said active ingredient.

12. A medicament in dosage unit form comprising an antibacterially effective amount of a compound according to claim 1 and an inert pharmaceutical carrier.

13. A medicament of claim 12 in the form of tablets, pills, dragees, capsules, ampules or suppositories.

14. A method of combating bacterial infection in warm-blooded animals which comprises administering to said animals an antibacterially effective amount of a compound according to claim 1 either alone or in admixture with a diluent or in the form of a medicament.

15. A method according to claim 14 in which the active compound is administered orally or parenterally.

* * * * *

UNITED STATES PATENT AND TRADEMARK OFFICE
CERTIFICATE OF CORRECTION

PATENT NO. : 4,559,342
DATED : December 17, 1985
INVENTOR(S) : Uwe Petersen, et al.

It is certified that error appears in the above-identified patent and that said Letters Patent is hereby corrected as shown below:

| | |
|---|---|
| Col. 6, line 42 | Right side of formula delete "MeOEt" and substitute --MgOEt₂-- |
| Col. 9, line 29 | Before structure insert --(Liebigs Ann. Chem. 677, 8 (1964)).-- |
| Col. 10, line 2 | After "O°" insert --C.-- |
| Col. 11, line 6 | After "1" first instance insert -- - -- |
| Col. 11, line 9 | After "cyanomethyl" delete "-" second instance |
| Col. 19, line 8 | Delete "7-14-(2" and substitute -- 7-[4-(2- -- |
| Col. 20, line 35, Ex. 24 | Delete beginning of formula and substitute: 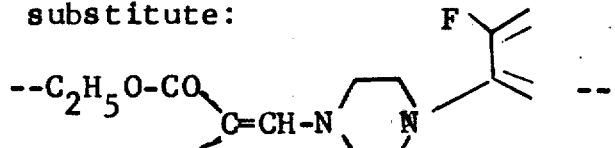 |
| Col. 21, lines 35-40 | In each instance delete " $\stackrel{<}{=}$ " and substitute -- $\leq$ -- |

Signed and Sealed this

Twenty-ninth Day of April 1986

[SEAL]

Attest:

DONALD J. QUIGG

Attesting Officer  Commissioner of Patents and Trademarks